(12) United States Patent
Nordström et al.

(10) Patent No.: US 8,938,047 B2
(45) Date of Patent: Jan. 20, 2015

(54) SEQUENCING SECTOR FIELDS

(75) Inventors: Håkan Nordström, Sollentuna (SE); Jonas Johansson, Uppsala (SE)

(73) Assignee: Elekta AB (Publ), Stockholm (SE)

( * ) Notice: Subject to any disclaimer, the term of this patent is extended or adjusted under 35 U.S.C. 154(b) by 369 days.

(21) Appl. No.: 13/518,356

(22) PCT Filed: Dec. 22, 2010

(86) PCT No.: PCT/EP2010/070468
§ 371 (c)(1),
(2), (4) Date: Aug. 22, 2012

(87) PCT Pub. No.: WO2011/076836
PCT Pub. Date: Jun. 30, 2011

(65) Prior Publication Data
US 2013/0178688 A1  Jul. 11, 2013

(30) Foreign Application Priority Data
Dec. 22, 2009  (EP) .................................. 09180468

(51) Int. Cl.
*A61N 5/10*  (2006.01)
*G21K 5/00*  (2006.01)

(52) U.S. Cl.
CPC .............. *A61N 5/103* (2013.01); *A61N 5/1084* (2013.01); *A61N 5/1078* (2013.01); *A61N 5/1031* (2013.01)
USPC ................................ 378/65; 378/64; 378/147

(58) Field of Classification Search
USPC ................. 378/64, 65, 147; 250/492.1, 492.3
See application file for complete search history.

(56) References Cited

U.S. PATENT DOCUMENTS

| 2004/0184577 A1* | 9/2004 | Carlsson et al. ................ 378/65 |
| 2010/0094119 A1* | 4/2010 | Yu et al. ........................ 600/411 |
| 2010/0288916 A1* | 11/2010 | Cho et al. ................... 250/252.1 |

FOREIGN PATENT DOCUMENTS

| WO | WO 2009/137010 A2 | 11/2009 |
| WO | WO 2009137010 A2 * | 11/2009 |

OTHER PUBLICATIONS

Wu and Bourland, "Morphology Guided Radiosurgery Treatment Planning", Medical Physics, vol. 26 No. 10, Oct. 1999, 2151-2160.*

(Continued)

*Primary Examiner* — Robert Kim
*Assistant Examiner* — David E Smith
(74) *Attorney, Agent, or Firm* — Birch, Stewart, Kolasch & Birch, LLP

(57) ABSTRACT

A method for planning a treatment session of a patient and optimizing the treatment time for a treatment using a radiation therapy system includes a radiation therapy unit having a fixed radiation focus point. During an optimization of a treatment plan for a patient, a set of shots to be delivered to a plurality of isocenter positions within a target volume of a patient during a treatment session are determined and a beam-on time for each respective sector and state for each isocenter during which radiation is to be delivered are determined based on the treatment plan. For each isocenter position, sectors and states of respective sector are grouped in accordance predetermined rules with respect to beam-on times for respective state of the sectors, wherein sectors and respective states are aggregated for simultaneous delivery of radiation during a predetermined period of time.

8 Claims, 6 Drawing Sheets

(56) References Cited

OTHER PUBLICATIONS

Li et al., "A constrained tracking algorithm to optimize plug patterns in multiple isocenter Gamma Knife radiosurgery planning." Medical Physics, vol. 32, No. 10, Sep. 23, 2005, pp. 3132-3135.

Ma et al., "A simple and effective method for validation and measurement of collimator output factors for Leksell Gamma Knife® Perfexion™." Physics in Medicine and Biology, vol. 54, No. 12, Jun. 21, 2009, pp. 3897-3907.

Wu et al., "Morphology-guided radiosurgery treatment planning and optimization for multiple isocenters." Medical Physics, vol. 26, No. 10, Oct. 1999, pp. 2151-2160.

* cited by examiner

SEQUENCING SECTOR FIELDS

FIELD OF THE INVENTION

The present invention relates to the field of radiation therapy. In particular, the invention relates to a method for planning a treatment session of a patient and optimizing the treatment time for a treatment using a radiation therapy system comprising a radiation therapy unit having a fixed radiation focus point.

BACKGROUND OF THE INVENTION

The development of surgical techniques have made great progress over the years. For instance, for patients requiring brain surgery, non-invasive surgery is now available which is afflicted with very little trauma to the patient.

One system for non-invasive surgery is the Leksell Gamma Knife® Perfexion system, which provides such surgery by means of gamma radiation. The radiation is emitted from a large number of fixed radioactive sources and is focused by means of collimators, i.e. passages or channels for obtaining a beam of limited cross section, towards a defined target or treatment volume. The collimator comprises a number of sectors where each sector may be set in a number of different states or collimator passage diameters. Typically, a collimator comprises eight sectors and each sector can be set in four different radiation states (beam-off, 4 mm, 8 mm, and 16 mm). It is possible to individually adjust the sectors, i.e. select a specific state for a specific sector, to change a spatial dose distribution surrounding the focus point, which is the point of convergence focused by the collimator.

Treatment planning optimization for radiation therapy, including for example gamma knife radiosurgery, aims providing a sufficient dose to the target volume within the patient (e.g. in treatment of tumours) at the same time as the dose delivered to adjacent normal tissues is minimized in order to spare healthy tissue and organs. In treatment planning optimization, the delivered radiation dose is limited by two competing factors where the first one is delivering a maximum dose to the target volume and the second one is delivering the minimum dose to the surrounding normal tissues.

A further important parameter which has to be taken into account is the total treatment time. The treatment planning optimization will result in a number of isocenters and for each isocenter, the position of the shot within the target volume to be treated as well as the beam-on time for each sector and for each state of each isocenter. Typically, the beam-on time for the eight different sectors and the four states (beam off, 4 mm, 8 mm, and 16 mm) are determined for each isocenter. A treatment including irradiation with each sector in each state of each isocenter would, in most cases, lead to very long irradiation times and thereby very long treatment times, which is uncomfortable for the patient, leads to a low patient flow and may, in addition, have adverse biological effects due to the low average doserate of the dose delivery.

Accordingly, there is need for more efficient methods and procedures for increasing the quality of the optimized treatment plan by shortening the treatment time.

SUMMARY OF THE INVENTION

Thus, an object of the present invention is to obtain more efficient methods and procedures for increasing the quality of the optimized treatment plan by shortening the treatment time.

This and other objects are fulfilled by the present invention as defined by the independent claims. Preferred embodiments are defined by the dependent claims.

The present invention is, for example, used in connection with treatment planning of treatment provided by means of a radiation therapy system having a collimator body provided with groups or sets of collimator passages, each set being designed to provide a radiation beam of a respective specified cross-section toward a fixed focus. Suitably the inlet of each set of collimator passages has a pattern that essentially corresponds to the pattern of the sources on the source carrier arrangement. These sets of collimator passage inlets may be arranged so that when the sources are displaced it is possible to change from one set to another, thereby changing the resulting beam cross-section and the spatial dose distribution surrounding the focus. The number of sets of collimator passages with different diameter may be more than two, such as three or four, or even more. A typical embodiment of the collimator comprises eight sectors each having four different states (beam-off, 4 mm, 8 mm, and 16 mm). The sectors can be adjusted individually, i.e. different states can be selected for each sector, to change the spatial distribution of the radiation about the focus point.

The term "target volume" refers to a representation of a target of a patient to be treated during radiation therapy. The target may be a tumour to be treated with radiation therapy. Typically, the representation of the target is obtained by, for example, non-invasive image capturing using X-ray or NMR.

The term "shot" refers to a delivery of radiation to a predetermined position within a target volume having a predetermined level of radiation and a spatial distribution. The shot is delivered during a predetermined period of time ("beam-on" time) via at least one sector of the collimator of the therapy system using different states for different sectors. A "composite shot" refers to the delivery of radiation to a focus point using different states (in the sense discussed above) for different sectors.

The term "beam-on time" refers to the predetermined period of time during which a shot is delivered to the target volume.

According to an aspect of the present invention, there is provided a method for a radiation therapy system. The system comprises a radiation therapy unit having a fixed radiation focus point, wherein a collimator of said therapy system is provided a plurality of collimator passage inlets directing radiation emanating from radioactive sources of a source carrier arrangement of the therapy system to said focus point, said collimator having a plurality of sectors and wherein each sector has a number of states of collimator passage diameters which can be individually adjusted to change spatial dose distribution surrounding the focus point. The method comprises, during an optimization of a treatment plan for patient, determining a set of shots to be delivered to a plurality of isocenter positions within a target volume of a patient during a treatment session and determining a beam-on time for each respective sector and state for each isocenter during which radiation is to be delivered based on the treatment plan. Further, for each isocenter position, sectors and states of respective sector are grouped in accordance predetermined rules with respect to beam-on times for respective state of the sectors, wherein sectors and respective states are aggregated for simultaneous delivery of radiation during a predetermined period of time.

According to a second aspect of the present invention, there is provided a software and/or hardware implemented sector planning module for a radiation therapy system. The system comprises a radiation therapy unit having a fixed radiation focus point, wherein a collimator of said therapy system is provided a plurality of collimator passage inlets directing radiation emanating from radioactive sources of a source carrier arrangement of the therapy system to said focus point, said collimator having a plurality of sectors and wherein each sector has a number of states of collimator passage diameters which can be individually adjusted to change spatial dose distribution surrounding the focus point. The sector planning module comprises a dose distribution module adapted to obtain information of a set of dose distributions to be delivered to a plurality of isocenter positions within a target volume of a patient during a treatment session and information of a beam-on time for each respective sector and state for each isocenter during which radiation is to be delivered based on the treatment plan. Further, an aggregation module is adapted to, for each isocenter position, group sectors and states of respective sector in accordance predetermined rules with respect to beam-on times for respective state of the sectors, wherein sectors and respective states are aggregated for simultaneous delivery of radiation during a predetermined period of time.

Hence, the present invention is based on the idea of, starting from the treatment plan, grouping sectors with the different states for simultaneous delivery of radiation. More specifically, the beam-on time for each composite shot (a composite shot is a shot delivered by means of several sectors, where the sectors may have different states, simultaneously) is maximized in order to minimize the total beam-on time. The sectors are thus aggregated for simultaneous delivery of dose to an isocenter and the aim is to include as many sectors as possible in each composite shot. Thereby, it is possible to significantly reduce the treatment time. Normally, the optimization procedure (of the treatment plan) results in a number of isocenters (locations for a shot within the target volume). For each isocenter, a position and the beam-on time for each of the sectors (e.g. eight) and for each state of respective sector (e.g. 4 mm, 8 mm, and 16 mm) are obtained. Irradiation with each sector in each state of each isocenter would generally lead to very long treatment times, which is uncomfortable for the patient. Further, it leads to low patient flow and may also have an adverse biological effect due to the low average dose-rate of the dose delivery. For example, the patient flow can be improved due to the reduced treatment times. In addition, the patient will experience a more convenient treatment procedure. Further, the treatment time can be significantly reduced and the radiobiological response can potentially be improved.

According to an embodiment of the present invention, the predetermined rules comprise selecting the longest beam-on time for each state of respective sector for an aggregated simultaneous delivery of radiation.

In one embodiment of the present invention, the predetermined period of time for simultaneous delivery of radiation is determined to be the minimum beam-on time for a state of a sector of the aggregated sectors, i.e. the minimum time for the maximum of times for each sector.

According to an embodiment of the present invention, it is checked whether the minimum beam-on time for a state of a sector of the aggregated sectors is zero. If a sector is found to have a zero beam-on time, that specific sector having a zero beam-on time is set to be blocked, wherein the sector is blocked for delivery of radiation; and the shortest non-zero beam-on time is selected as the period of time for delivery of radiation.

In an embodiment of the present invention, a set of sectors and respective states aggregated for a simultaneous delivery of radiation during a predetermined period of time is excluded from delivery if said predetermined period of time is below a predetermined threshold. Thus, a composite shot is excluded from delivery of radiation if the delivery time or beam on time is below or equal to a predetermined threshold, for example, below or equal to 1 or 2 seconds. Thereby, the total treatment time can be reduced even further without compromising on the quality of the treatment since the additional treatment effect provided by this very short treatment times are, in an overall perspective, more or less negligible.

As the skilled person realizes, steps of the methods according to the present invention, as well as preferred embodiments thereof, are suitable to realize as computer program or as a computer readable medium.

Further objects and advantages of the present invention will be discussed below by means of exemplifying embodiments.

DETAILED DESCRIPTION OF THE DRAWINGS

Figure 1:
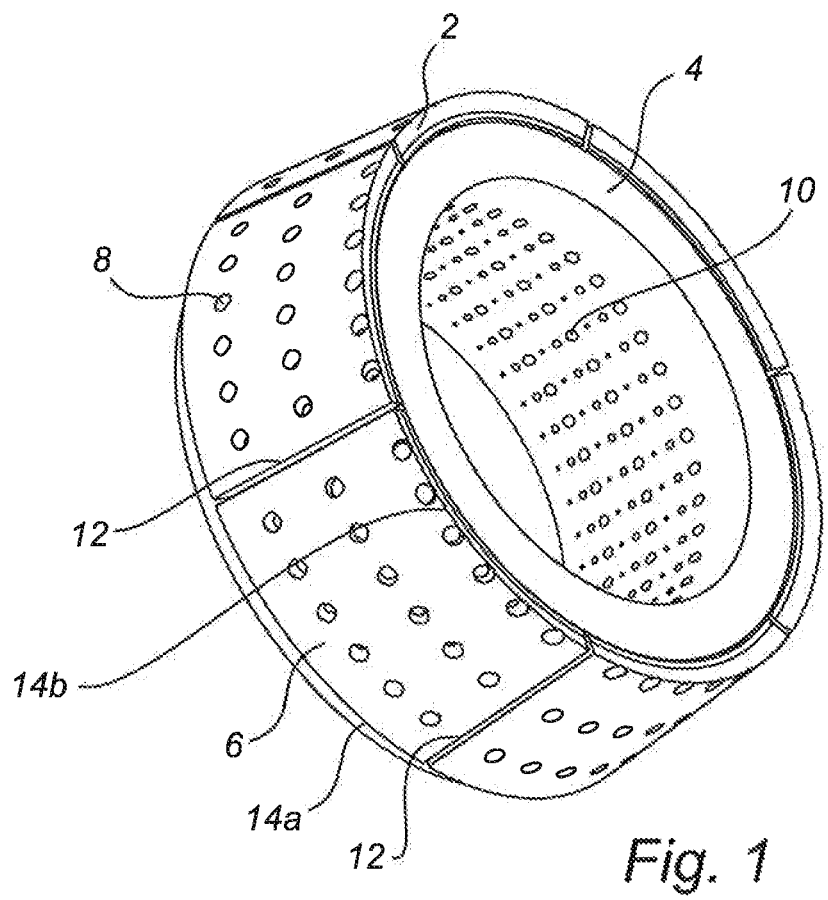
FIG. 1 is a perspective view of an assembly comprising a source carrier arrangement surrounding a collimator body, in accordance with an embodiment of the invention.

With reference to FIGS. 1-5, an exemplary radiation therapy device in which a treatment plan developed using the present invention can be used for treatment of a patient. FIG. 1 is a perspective view of an assembly comprising a source carrier arrangement 2 surrounding a collimator body 4. The source carrier arrangement 2 and the collimator body 4 both have the shape of a frustum of a cone. The source carrier arrangement 2 comprises six segments 6 distributed along the annular circumference of the collimator body 4. Each segment 6 has a plurality of apertures 8 into which containers containing radioactive sources, such as cobalt, are placed. The collimator body 4 is provided with collimator passages or channels, internal mouths 10 of said channels are shown in the figure.

Each segment 6 has two straight sides 12 and two curved sides 14a, 14b. One of the curved sides 14a forms a longer arc of a circle, and is located near the base of the cone, while the other curved side 14b forms a shorter arc of a circle. The segments 6 are linearly displaceable, that is they are not rotated around the collimator body 4, but are instead movable back and forth along an imaginary line drawn from the center of the shorter curved side 14b to the center of the longer curved side 14a. Such a translation displacement has the effect of a transformation of coordinates in which the new axes are parallel to the old ones.

As can be seen from FIG. 1 there is a larger number of internal mouths 10 or holes of the collimator passages than the number of apertures 8 for receiving radioactive sources. In this particular case there are three times as many collimator passages as there are apertures for receiving radioactive sources, such as e.g. 180 apertures and 540 collimator passages. The reason for this is that there are three different sizes of collimator passages in the collimator body 4, or rather passages which direct radiation beams with three different diameters, toward the focus. Said diameters may e.g. be 4, 8 and 16 mm. The three different types of collimator passages are each arranged in a pattern which corresponds to the pattern of the apertures in the source carrier arrangement. The desired size or type of collimator passage is selected by displacing the segments 6 of the source carrier arrangement linearly along the collimator body so as to be in register with the desired collimator passages.

Figure 2:
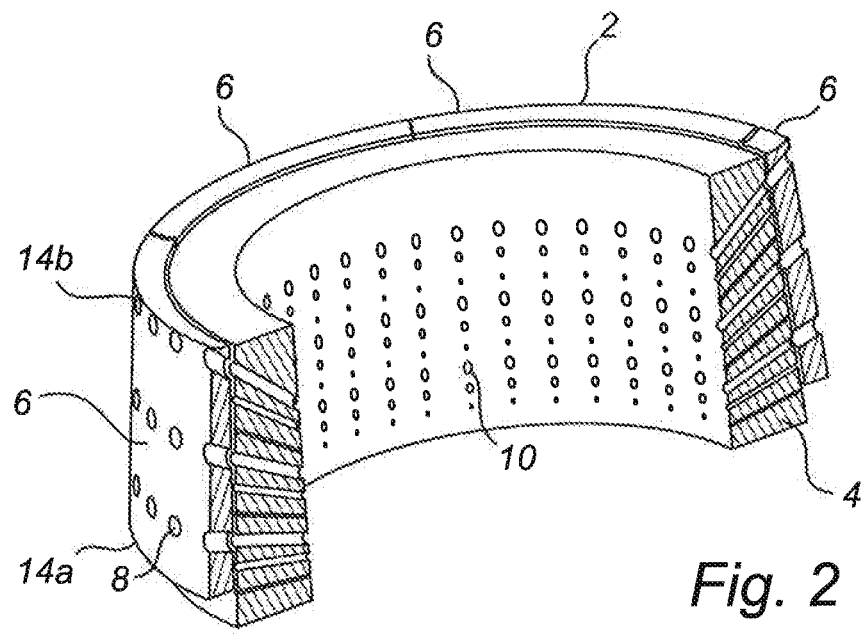
FIG. 2 is sectional view in perspective of the assembly shown in FIG. 1.

FIG. 2 is sectional view in perspective of the assembly shown in FIG. 1. The same reference numerals are used for details which are the same as in FIG. 1. This also applies to the following FIGS. 3 and 4.

Figure 3:
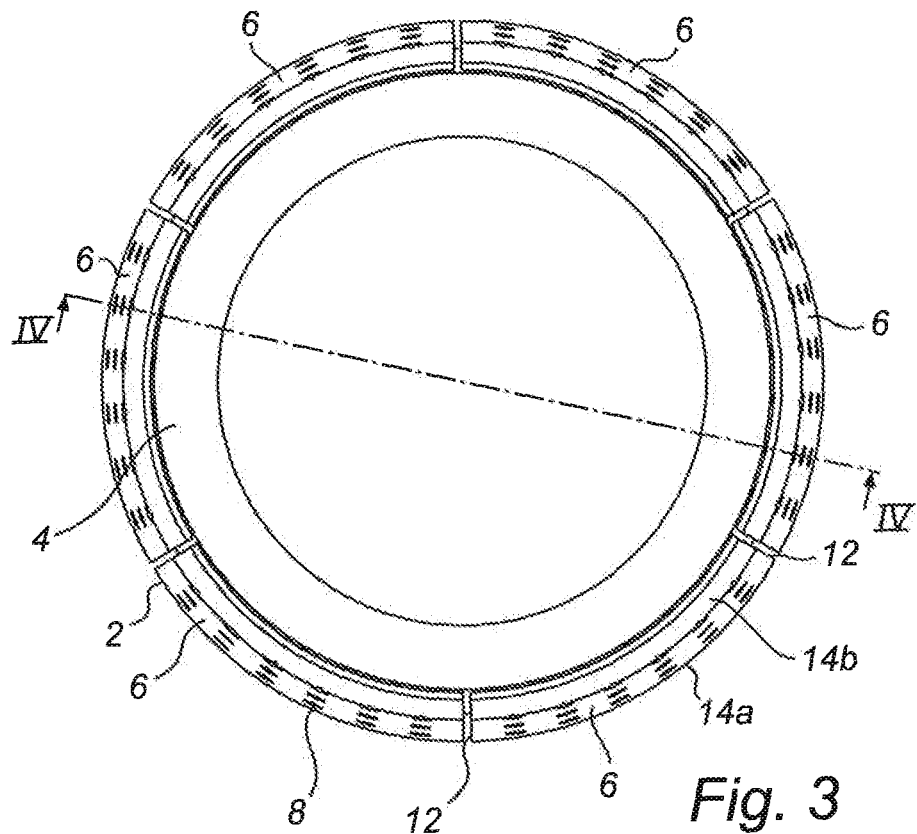
FIG. 3 is a view from the backside of the assembly shown in FIG. 1.

FIG. 3 is a view from the backside of the assembly shown in FIG. 1. This is the side with smaller diameter, while the other side, having a larger diameter, is the front or patient side, i.e. where the patient's body is introduced.

Figure 4:
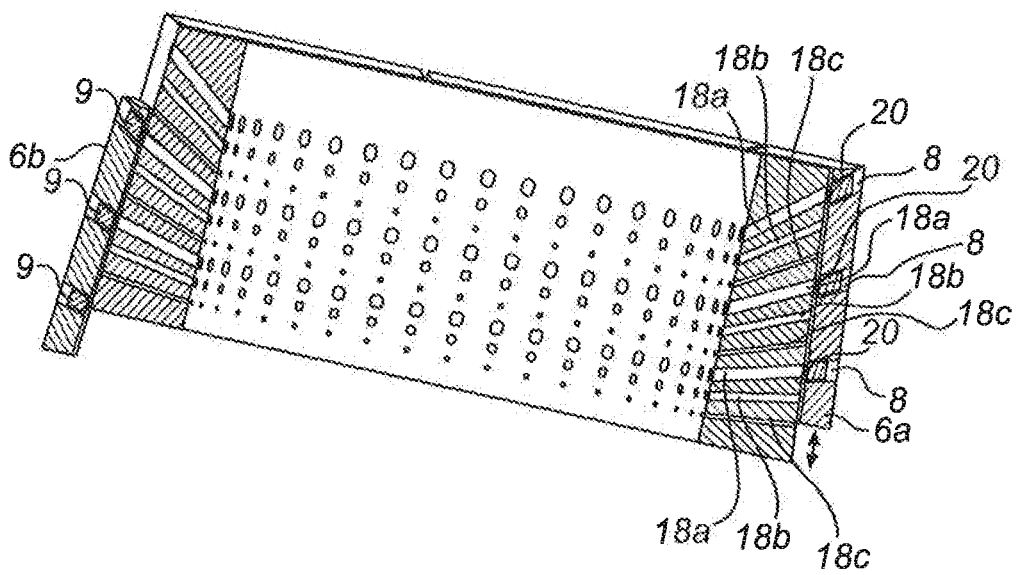
FIG. 4 is a view in cross-section along line IV-IV in FIG. 3.

FIG. 4 is a view in cross-section along line IV-IV in FIG. 3. Thus, in FIG. 4 two segments 6a and 6b are shown. Starting with one of the segments 6a, in this view it can be seen that there are nine collimator passages 18a-18c available for three radioactive sources 9 contained in a respective aperture 8 in the source carrier arrangement. The sizes of the collimators 18a-18c are arranged in an alternating sequence, such as for instance, the first collimator passage 18a providing a beam of 16 mm in diameter, the second collimator passage 18b providing a beam of 8 mm in diameter, the third collimator passage 18c providing a beam of 4 mm in diameter, the fourth collimator passage 18a starting the sequence all over by providing a beam of 16 mm in diameter, etc. However, the collimator passages 18a-18c could, alternatively, be arranged in another order, e.g. to provide the sequence 16 mm, 4 mm, 8 mm. In the figure the apertures 8 of the source carrier arrangement are arranged in register with the first, fourth and seventh collimator passages 18a, or rather their respective inlets, said collimator passages all providing a beam of 16 mm in diameter at the focus. Each segment may be individually displaced in a straight direction as is illustrated with the double-headed arrow in order to select another group of collimator passages, i.e. another beam diameter size for any segment. If the segment is displaced so that the radioactive sources 9 face a surface in between the collimator passages, those radioactive sources will be shut off, i.e. essentially no or only a minimum radiation from those sources will reach the focus. A segment may also like the segment 6b in FIG. 4 be displaced to such an extent that one of the three shown apertures will be located beside and outside of the first or ninth collimator passage. This allows of the possibility to arrange only two of the three radiation sources 9 in register with two collimator passages.

As can be seen in FIG. 4 the nine collimator passages 18a-18c are arranged at somewhat different angles in order for the beams to be directed to the common focus, regardless of which collimator passage or passages that are used at the moment. The angle of extension direction of the first to the last collimator passage having the same cross-section is, in this case, at least 30°.

Figure 5:
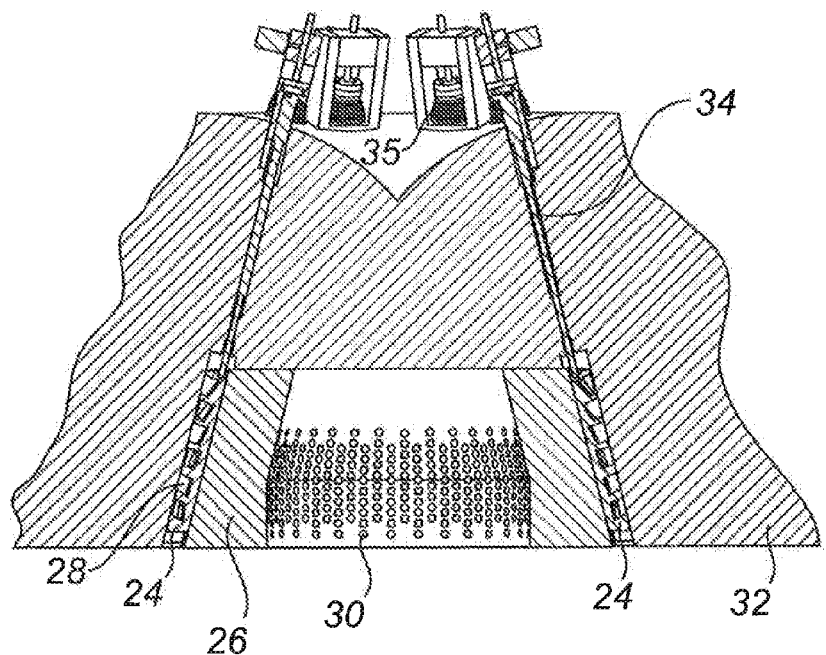
FIG. 5 is a sectional view of an assembly of the type shown in FIGS. 1-4, said assembly being illustrated with an actuating mechanism and a rear radiation protection structure.

FIG. 5 is a sectional view of an assembly of the type shown in FIGS. 1-4, said assembly being illustrated with an actuating mechanism and a rear radiation protection structure. Accordingly, a source carrier arrangement having a plurality of segments 24 is provided. Each segment 24 has a number of apertures 28 in which sources are inserted. The segments 24 are arranged around a collimator body 26 having collimator passages (not shown) with mouths 30 directing radiation beams towards a focus.

The segments are surrounded by a rear radiation protection structure 32, so as to minimize or eliminate leakage of radiation to the nursing personnel. The rear protection structure 32 is dimensioned and made of a suitable material, such as casting material, accordingly. A front radiation protection structure (not shown) is suitably also provided, preferably of smaller dimension so as to facilitate access to the treatment space, but with a high density material, such as lead, tungsten or depleted uranium.

An actuating mechanism is provided for displacing the segments in a linear direction of motion. The maximum displacement distance for a segment may e.g. be 60 mm, however larger or smaller distances are also conceivable. The actuating mechanism comprises a number of supporting rods or arms 34, each arm being connected to a respective segment 24. The arms 34 extend through a respective bore in the rear radiation protection structure 32 and are movable along their direction of elongation. The arm and the bore are designed so as to form a labyrinth passage having different portions of overlapping diameters, thereby minimizing or eliminating the escape of hazardous radiation through the bore. Each arm is individually controlled by means of a respective rotational electrical motor. The electrical motor has a high resolution with a positioning encoder and a ball roller screw enabling a precise linear positioning of the arm 34 and the segment 24. A spring means 35 is arranged to affect the arms and ensure that they displace the segments so that the radioactive sources will be in a complete shut-off position (i.e. shielded position) in case of power failure. The arms 34 may be disconnected from the segments 24, when the segments are to be provided with new radioactive sources. In such case the loading is suitably done through channels (not shown) provided in one area of in the rear radiation protection structure 32. The loading procedure may be performed in a conventional manner as in the prior art, e.g. a procedure corresponding to the one used in connection with Leksell Gamma Knife® Perfexion. However, alternative procedures are also conceivable.

Figures 6A, 6B, 6C:
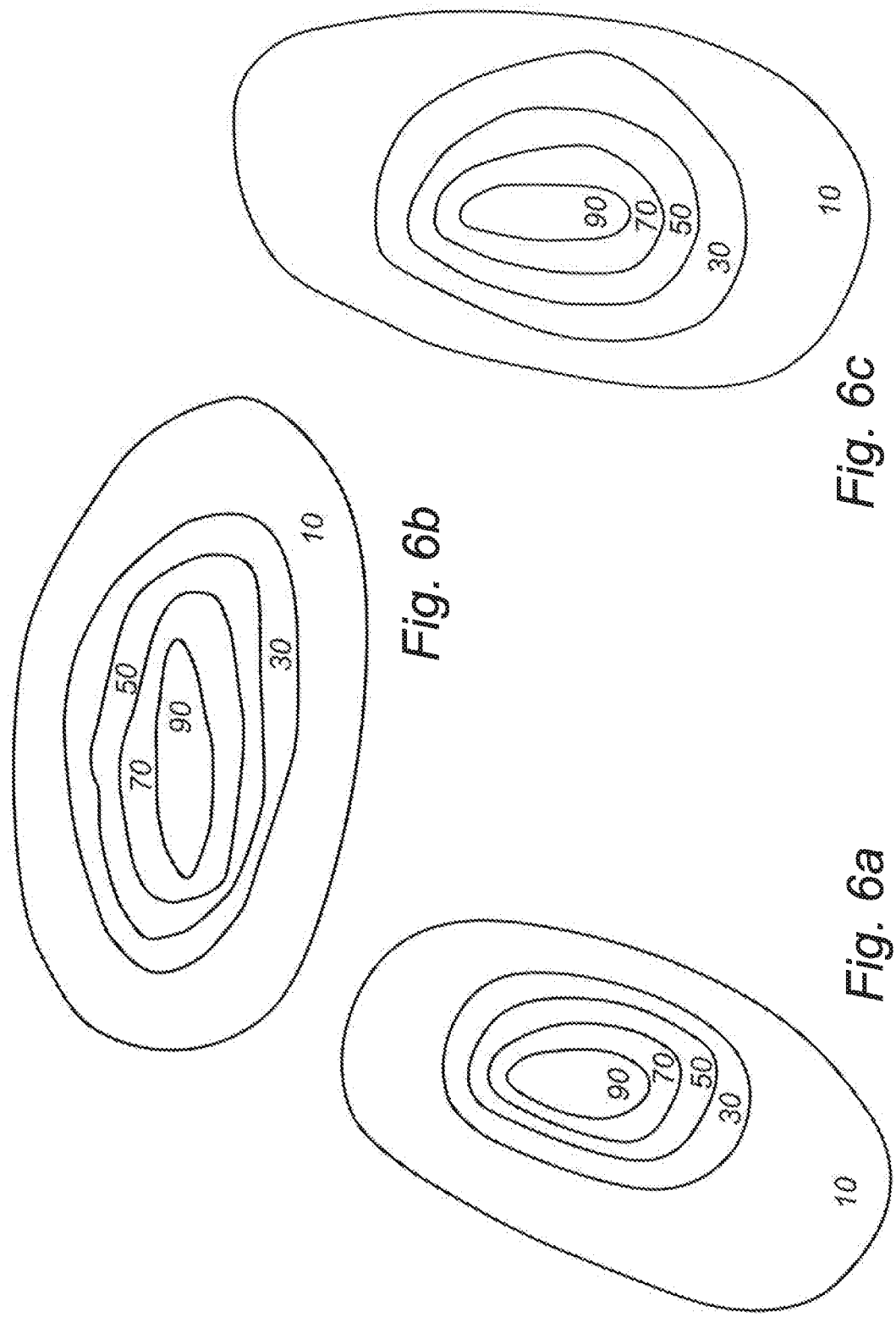
FIGS. 6a-6c show schematic representations of the dose distribution in three central planes of an example of a composite shot.

In FIG. 6a-6c, the dose distributions along a central plane for a single composite shot (i.e. using different collimator sizes in different sectors) are shown. The high dose levels are confined to small regions and the surrounding region exhibits a limited dose. In general, for a larger or irregular target shape, multiple shots have to be used to cover the target region. Generally, the optimization procedure results in a number of isocenters and for each isocenter, the position as well as the beam-on time for each of the eight different sectors and each state (4 mm, 8 mm, and 16 mm) of each isocenter. However, irradiating with each sector in each state of each isocenter would generally lead to very long irradiation times which are uncomfortable for the patient. These long irradiation times also lead to low patient flows and may have an adverse biological effect. The present invention includes a method according to which sector fields are grouped into sets of composite shots where as many sectors as possible are used in each composite shot (i.e. every moment dose is delivered to an isocenter).

The costs function in inverse planning in radiotherapy or radiosurgery is, in principle, always dependent on the physical dose delivered to a target. The dose at a point $\vec{x}$ may be written according to the following:

$$D(\vec{x}) = \sum_{i=1}^{N_{ISO}} \sum_{\mu=1}^{24} w_i^\mu \phi_\mu(\vec{x}, \vec{\xi}_i) \quad (1)$$

Here, $\vec{\xi}_i$ is the isocenter position i, $w_i^\mu, \phi_\mu(\vec{x}, \vec{\xi}_i)$ are the beam-on time and dose-rate kernel for isocenter position i and for sector and state combination μ, respectively. In a radiation system having eight sectors and three states (collimator passage diameters) μ will range from 1 to 24. Assuming that the isocenter positions are fixed (e.g. by having defined a grid of delivery points in a position space), the beam-on times can be determined. The total beam on time T can be determined by summing the beam on time for each sector and each state according to:

$$T = \sum_{i=1}^{N_{ISO}} \sum_{\mu=1}^{24} w_i^\mu \quad (2)$$

As understood, this will lead to very long treatment times leading to inter alia significant discomfort for the patient.

According to the invention, the sectors are aggregated in so called "meta shots" instead of delivering the radiation sector by sector. A meta shot is a set of different composite shots at a given isocenter position. The invention aims at maximizing the beam-on time of every composite shot to ensure a short delivery time. The algorithm can be generalized as follows. For a single isocenter, the weight $w_\mu$, $\mu=1, \ldots, 24$, the weight may be presented as the following matrix:

$$T_s^i = \begin{pmatrix} t_1^1 & t_2^1 & \ldots & \ldots t_8^1 \\ t_1^2 & t_2^2 & \ldots & \ldots t_8^2 \\ t_1^3 & t_2^3 & \ldots & \ldots t_8^3 \end{pmatrix}$$

The algorithm identifies for each sector the state having the longest beam-on time. Among these states, the algorithm finds the state with the shortest beam on time, $\tau_k$. The states with the longest beam-on time will constitute a composite state, $CS_k$ with the beam-on time $\tau_k$. Then $\tau_k$ is subtracted from $T_s^i$ for the sector states with the longest beam-on time and a new $T'^i_s$ is obtained. This procedure is repeated until there are no sectors that have a non-zero beam-on time. Thus, the result will be a set of composite shots $(\tau_k, CS_k)$, where $k=1 \ldots M_i$ at each isocenter i.

Figure 7:
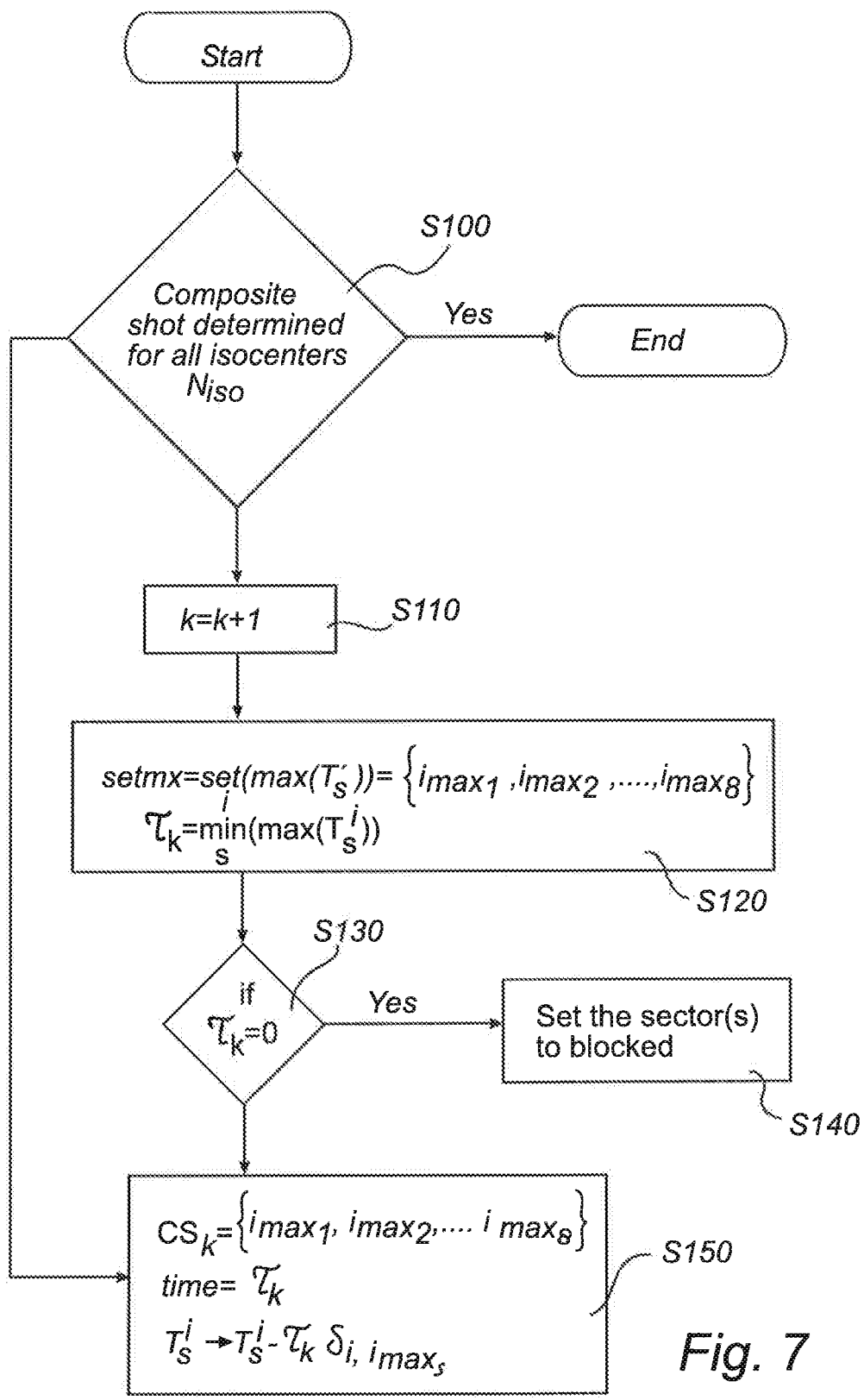
FIG. 7 is a flow chart illustrating an embodiment of the method according to the present invention.

The algorithm is illustrated in a block diagram shown in FIG. 7. At step S100, it is checked whether a set of composite shot has been determined for all isocenters i=1, . . . $N_{ISO}$. If no, the algorithm proceeds to step S110 and, if yes, the algorithm is terminated. Hence, if it is determined at step S100 that the composite set has not been determined for isocenter i, the following steps S110-S150 will be executed to determine a composite set for that specific isocenter. At step S110, it is determined that the beam-on time for state k=k+1 should be checked. Then, at step S120, a set of the maximum beam-on times is identified. That is, for each sector the longest beam-on time is identified. Further, among these beam-on times $i_{max1}$-$i_{max8}$, the shortest beam-on time is identified $\tau_k$.

Thereafter, at step S130, it is checked whether $\tau_k$=0. If $\tau_k$=0, the algorithm proceeds to step S140 where the sector (-s) is (are) set to blocked. That is, a sector or a number of sectors are excluded from delivery of radiation.

On the other hand, if $\tau_k \neq 0$, the procedure proceeds to step S150, where composite state $CS_k$ with the beam-on time $\tau_k$ is formed. Thereafter, the algorithm returns to step S100 where a new check whether a composite shot has been determined for all isocenters The principles of the algorithm described above will now be explained by means of a simplified example. Let us assume a treatment system having only two sectors S1 and S2 each having two states A and B. Let us further assume that we, after optimization of the treatment plan, have the following configuration:

| S1 | | S2 | |
|---|---|---|---|
| A | B | A' | B' |
| 6 s | 10 s | 13 s | 4 s |

If the dose would be delivered sector by sector, the total treatment time would be 6 s+10 s+13 s+4=33 s.

If we instead utilize the ideas of the present invention to aggregate the sectors into composite shots only 17 seconds will be required. That is, a significant reduction of the total treatment time can be achieved as will be shown below. In this simplified example, a reduction of the treatment time of 49% was achieved.

First, the longest beam-on time for each sector is identified, which is 10 s for state B and 13 s for state A', respectively. The minimum time of this set is 10 s. Hence, the composite shot is:

| S1 | S2 | Time |
|---|---|---|
| B | A' | 10 s |

Then, the configuration will be as follow:

| S1 | | S2 | |
|---|---|---|---|
| A | B | A' | B' |
| 6 s | 0 s | 3 s | 4 s |

Again, the longest beam-on time for each sector is identified, which now is 6 s for state A and 4 s for state B', respectively. The minimum time of this set is 4 s. Hence, the next composite shot is:

| S1 | S2 | Time |
|---|---|---|
| A | B' | 4 s |

The configuration will be as follow:

| S1 | | S2 | |
|---|---|---|---|
| A | B | A' | B' |
| 2 s | 0 s | 3 s | 0 s |

The algorithm is repeated again. The longest beam-on time for each sector is identified, which now is 2 s for state A and 3 s for state A', respectively. The minimum time of this set is 4 s. Hence, the next composite shot is:

| S1 | S2 | Time |
|----|----|------|
| A  | A' | 2 s  |

Now, the configuration will be as follow:

| S1 | | S2 | |
|----|----|----|----|
| A | B | A' | B' |
| 0 s | 0 s | 1 s | 0 s |

This time, the first sector S1 will be blocked since there are no irradiation times left for the states A and B. However, for sector S2, there is irradiation time for state A' left. The final composite shot will thus be:

| S1 | S2 | Time |
|----|----|------|
| OFF | A' | 1 s |

Thus, using the present invention, i.e. where the sectors are aggregated into composite shots, a total treatment time of 17 seconds is achieved in this specific example in comparison to the prior art technique, where sector by sector is used, which requires 33 seconds. This simplified example given above illustrates the overall principles of the present invention.

According to an embodiment of the present invention, a composite shot is excluded from delivery of radiation if the delivery time or beam on time is below or equal to a predetermined threshold, for example, below or equal to 1 or 2 seconds. Thereby, the total treatment time can be reduced even further without compromising on the quality of the treatment since the additional treatment effect provided by this very short treatment times are, in an overall perspective, more or less negligible.

Figure 8:
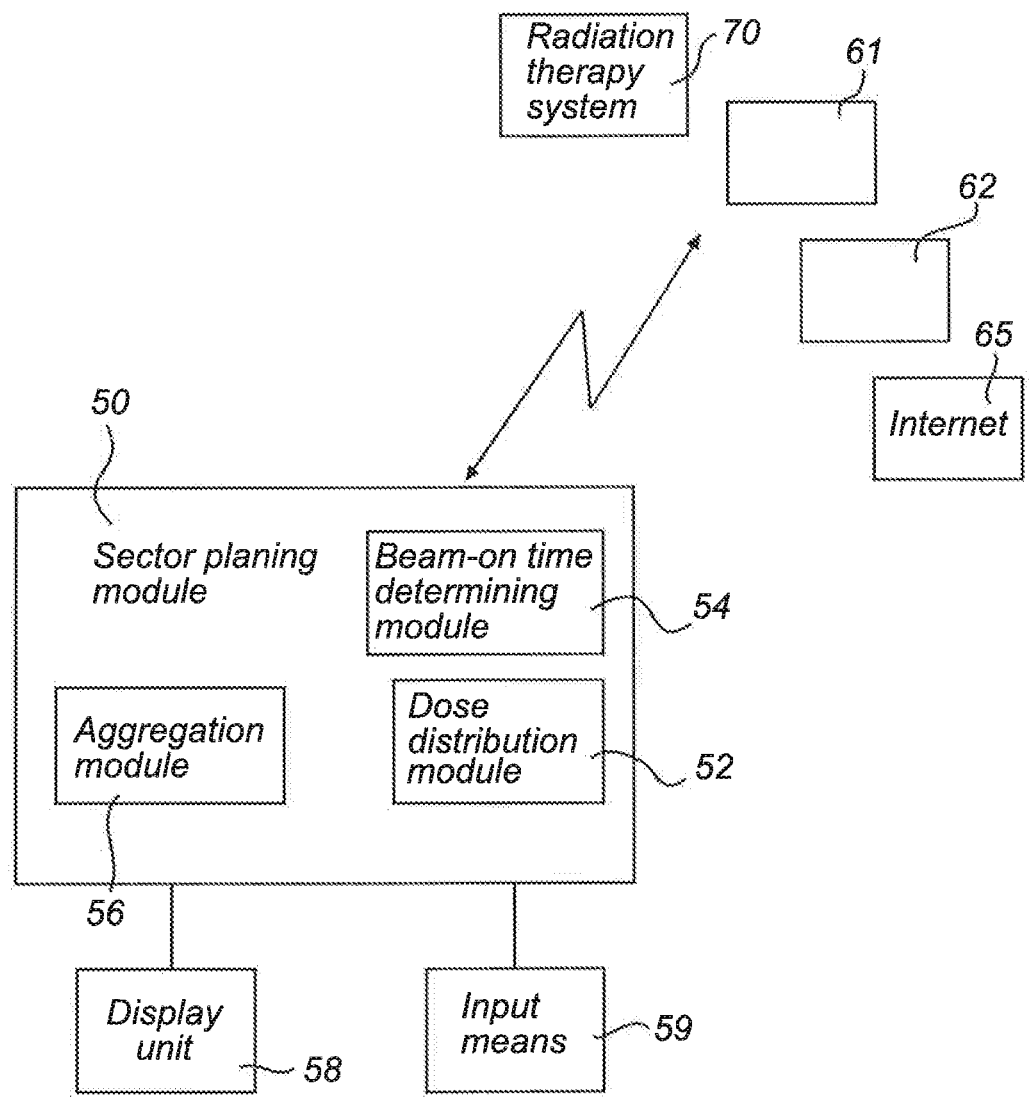
FIG. 8 is schematic illustration of an embodiment of a sector planning module according to the present invention.

Turning now to FIG. 8, an embodiment of a sector planning module according to the present invention will be discussed. A sector planning module 50 according to the present invention may, for example, be integrated in computer device such as a computerized system, a personal computer etc. provided with a display unit. The sector planning module 50 may be implemented as software modules including program instructions for executing a method according to the present invention, for example, a method as described above with reference to FIG. 7. The sector planning module 50 may alternatively be implemented as hardware modules. Further, the sector planning module 50 may be implemented as a combination of software and hardware modules.

A sector planning module 50 according to the present invention may, for example, be integrated in computer device such as a computerized system, a personal computer etc. provided with a display unit. The sector planning module 50 may be connected to other devices 61, 62 such as other personal computer, servers, medical systems etc at a hospital or care provider institution via a network 60, e.g. wirelessly by means of Bluetooth or via a cable network. Further, the sector planning module 50 may be connected to other networks such as the Internet 65.g. wirelessly by means of Bluetooth or via a cable network. A set of composite shots determined by the sector planning module 50 may be transferred to a radiation therapy system 70, for example, the radiation therapy system described above with reference to FIG. 1-5. For example, the set of composite shots may be transferred wirelessly via the network 60 to the radiation therapy system 70 for use in a treatment of the patient. The sector planning module 50 comprises a dose distribution module 52 adapted to obtain information of a set of shots to be delivered to a plurality of isocenter positions within a target volume of a patient during a treatment session determined during an optimization of a treatment plan. This information may be obtained from an optimization module of a device 61, 62, e.g. a computer, connected wirelessly to the sector planning module 50. Further, a beam-on time determining module 54 is adapted to determine a beam-on time for each respective sector and state for each isocenter during which radiation is to be delivered based on the treatment plan. Alternatively, this information may also be obtained by the dose distribution module 52 from an optimization module of a device 61, 62, e.g. a computer, connected wirelessly to the sector planning module 50. An aggregation module 56 is adapted to, for each isocenter position, group sectors and states of respective sector in accordance predetermined rules with respect to beam-on times for respective state of the sectors, wherein sectors and respective states are aggregated for simultaneous delivery of radiation during a predetermined period of time. A method for this has been described above with reference to FIG. 7. An operator or physician may input information to the aggregation module manually via input means 59 such as a keyboard and/or a mouse connected to the sector planning module or of a personal computer in which the sector planning module 50 is integrated. A composite shot can be excluded from delivery of radiation if the delivery time or beam on time is below or equal to the predetermined threshold, for example, below or equal to 1 or 2 seconds, which threshold the physician or operator may adjust manually. The physician or operator may also view result from the sector planning on a display unit 58 connected to the sector planning module 50 or of a computer in which the sector planning module 50 is integrated.

Although an exemplary embodiment of the present invention has been shown and described, it will be apparent to those having ordinary skill in the art that a number of changes, modifications, or alterations to the inventions as described herein may be made. Thus, it is to be understood that the above description of the invention and the accompanying drawings is to be regarded as a non-limiting.

The invention claimed is:

1. A method for optimizing a treatment plan for a patient for a gamma radiation therapy system, the system comprising a radiation therapy unit having a fixed radiation focus point, wherein a collimator of said therapy system is provided with a plurality of collimator passage inlets directing radiation emanating from radioactive sources of a source carrier arrangement of the therapy system to said focus point, said collimator having a plurality of sectors and wherein each sector has a number of states of collimator passage diameters which can be individually adjusted to change a spatial dose distribution surrounding the focus point, said method comprising the steps of:
   determining a set of shots to be delivered to a plurality of isocenter positions within a target volume of a patient during a treatment session;
   determining a beam-on time for each respective sector and state for each isocenter during which radiation is to be delivered based on the treatment plan; and
   for each isocenter position, grouping sectors and states of respective sector in accordance with predetermined rules with respect to beam-on times for respective states of the sectors,
   wherein sectors and respective states are aggregated for simultaneous delivery of radiation during a predetermined period of time, and wherein the predetermined rules comprise selecting the longest beam-on time for each state of a respective sector for an aggregated simultaneous delivery of radiation and wherein the predetermined period of time for simultaneous delivery of radiation is determined to be the minimum beam-on time for a state of a sector of the aggregated sectors.

2. The method according to claim 1, further comprising the steps of:
checking whether the minimum beam-on time for a state of a sector of the aggregated sectors is zero;
setting the sector having a zero beam-on time to be blocked, wherein the sector is blocked for delivery of radiation; and
selecting the shortest non-zero beam-on time as the period of time for delivery of radiation.

3. The method according to claim 2, further comprising the step of excluding a set of sectors and respective states aggregated for a simultaneous delivery of radiation during a predetermined period of time from delivery if said predetermined period of time is below a predetermined threshold.

4. The method according to claim 1, further comprising the step of excluding a set of sectors and respective states aggregated for a simultaneous delivery of radiation during a predetermined period of time from delivery if said predetermined period of time is below a predetermined threshold.

5. A sector planning module for a gamma radiation therapy system, the system comprising a radiation therapy unit having a fixed radiation focus point, wherein a collimator of said therapy system is provided with a plurality of collimator passage inlets directing radiation emanating from radioactive sources of a source carrier arrangement of the therapy system to said focus point, said collimator having a plurality of sectors and wherein each sector has a number of states of collimator passage diameters which can be individually adjusted to change a spatial dose distribution surrounding the focus point, said sector planning module comprising:
a dose distribution module adapted to obtain information of a set of shots to be delivered to a plurality of isocenter positions within a target volume of a patient during a treatment session, and of a beam-on time for each respective sector and state for each isocenter during which radiation is to be delivered based on the treatment plan; and
an aggregation module adapted to, for each isocenter position, group sectors and states of respective sector in accordance with predetermined rules with respect to beam-on times for respective states of the sectors,
wherein sectors and respective states are aggregated for simultaneous delivery of radiation during a predetermined period of time and wherein the predetermined rules comprise to select the longest beam-on time for each state of a respective sector for an aggregated simultaneous delivery of radiation and wherein the predetermined period of time for simultaneous delivery of radiation is determined to be the minimum beam-on time for a state of a sector of the aggregated sectors.

6. The sector planning module according to claim 5, whether said aggregation module is adapted to:
check whether the minimum beam-on time for a state of a sector of the aggregated sectors is zero;
set the sector having a zero beam-on time to be blocked, wherein the sector is blocked for delivery of radiation; and
select the shortest non-zero beam-on time as the period of time for delivery of radiation.

7. The sector planning module according to claim 6, wherein said aggregation module is adapted to exclude a set of sectors and respective states aggregated for a simultaneous delivery of radiation during a predetermined period of time from delivery if said predetermined period of time is below a predetermined threshold.

8. The sector planning module according to claim 5, wherein said aggregation module is adapted to exclude a set of sectors and respective states aggregated for a simultaneous delivery of radiation during a predetermined period of time from delivery if said predetermined period of time is below a predetermined threshold.

* * * * *